United States Patent [19]

Plant et al.

[11] 4,019,893
[45] Apr. 26, 1977

[54] HERBICIDAL METHOD USING 2-SULFINYL OR 2-SULFONYL PYRIDINE N-OXIDE DERIVATIVES

[75] Inventors: Howard L. Plant, Milford; Allyn Roy Bell, Cheshire, both of Conn.

[73] Assignee: Uniroyal Inc., New York, N.Y.

[22] Filed: Mar. 17, 1975

[21] Appl. No.: 559,188

[52] U.S. Cl. .................................. 71/94; 71/88; 71/90
[51] Int. Cl.² .......................................... A01N 9/22
[58] Field of Search ........................... 71/94, 98

[56] References Cited

UNITED STATES PATENTS

| | | | |
|---|---|---|---|
| 3,124,447 | 3/1964 | Wineman et al. | 71/98 |
| 3,141,907 | 7/1964 | Mark | 71/98 |
| 3,155,671 | 11/1964 | D'Amico | 71/94 |
| 3,295,946 | 1/1967 | D'Amico | 71/94 |
| 3,303,209 | 2/1967 | Reifschneider et al. | 71/98 |
| 3,705,170 | 12/1972 | Torba | 71/94 |

OTHER PUBLICATIONS

Walter et al., "Oxydationsreaktionen an Thiolimed etc.," (1966) Hebigs Ann. 695, pp. 77–86 (1966).

*Primary Examiner*—Glennon H. Hollrah
*Attorney, Agent, or Firm*—James J. Long

[57] ABSTRACT

Preemergence or postemergence control of weeds is effected by applying certain 2-sulfinyl or 2-sulfonyl pyridine N-oxide derivatives, e.g., 2-(4-chlorophenylmethylsulfonyl)pyridine N-oxide.

17 Claims, No Drawings

HERBICIDAL METHOD USING 2-SULFINYL OR 2-SULFONYL PYRIDINE N-OXIDE DERIVATIVES

Certain substituted 2-sulfinyl and 2-sulfonyl pyridine N-oxides disclosed herein are claimed as new compositions in our copending application Ser. No. 559,196 filed of even date herewith, now U.S. Pat. No. 3,960,542, issued June 1, 1976, and hereby incorporated herein by reference.

This invention relates to a method of controlling weeds.

W. Walter et al., Liebig's Ann., 695, 77 (1966), disclose 2(phenylmethylsulfinyl)pyridine N-oxide (also called 2-benzylsulfinylpyridine N-oxide) and 2-(phenylmethylsulfonyl)pyridine N-oxide (also called 2-benzylsulfonylpyridine N-oxide), but no utility for these chemicals is disclosed.

U.S. Pat. No. 3,107,994, Rawlings et al., Oct. 22, 1963, discloses certain herbicidal 2-(alkenylthio)pyridine N-oxides, while U.S. Pat. No. 3,155,671, D'Amico, Nov. 3, 1964, discloses certain herbicidal benzyl 2-thiopyridine N-oxides.

The state of the art is further illustrated by such references as E. Shaw et al., JACS 72, 4362 (1950) and U.S. Pat. No. 3,772,307, Kaminsky et al., Nov. 13, 1973.

Weeds compete with crops for light, moisture, nutrients and space. Thus, weeds inhibit the production of foliage, fruit or seed of agricultural crops. The presence of weeds may also reduce the quality of the harvested crop and reduce harvesting efficiency. Weed control is essential for maximum production of many agronomic and horticultural crops including soybeans (*Glycine max L.*), peanuts (*Arachis hypogaea L.*), flax (*Linum usitatissium*) (*L.*)), and cotton (*Gossypium sp.*).

In accordance with the invention, the undesirable effects of weeds are controlled by applying, to a locus at which weed control is desired, a herbicidally effective amount of a 2-sulfinyl or 2-sulfonyl pyridine N-oxide of the formula

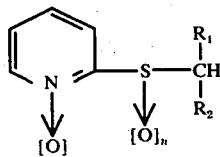

where
  $n$ is 1 or 2
  $R_1$ is hydrogen, alkyl having 1 to 3 carbon atoms or phenyl;
  $R_2$ has one of the following values when $R_1$ is hydrogen;
    cyclohexyl, 2,2-dichlorocyclopropyl, 2,2-dichloro-1-methylcyclopropyl, propenyl, benzyl, styryl, cyano, naphthyl, methylnaphthyl, pyridyl, benzothiazolyl, phenyl, substituted phenyl with 1 to 5 substituents which may be the same or different and selected from alkyl having 1 to 3 carbon atoms, halogen, nitro, cyano, alkoxy having 1 or 2 carbon atoms, methylenedioxy, 2,2-dichlorocyclopropyl and trifluoromethyl;
  $R_2$ has one of the following values when $R_1$ is otheer than hydrogen:
    alkyl having 1 to 4 carbon atoms, naphthyl, thienyl, phenyl, substituted phenyl with 1 to 3 substituents which may be the same or different and are selected from alkyl having 1 to 2 carbon atoms, halogen, nitro, and methyl-sulfonyl; and
  $R_1$ and $R_2$ may be connected together as a chain of methylene groups to form a cyclic aliphatic ring containing 5 to 7 carbon atoms.

Of particular interest in many cases are compounds of the above-defined class in which $R_1$ is hydrogen or methyl.

Also of special value are compounds of the above-defined formula in which $R_2$ is selected from the group consisting of phenyl, phenyl substituted with from 1 to 3 methyl groups, phenyl substituted with from 1 to 3 halogens, and 2-naphthyl.

Particular mention may be made of compounds as defined above in which $R_1$ is hydrogen and $R_2$ is selected from the group consisting of phenyl substituted with from 1 to 3 methyl groups and phenyl substituted with from 2 to 3 chlorines.

In another aspect the invention is directed to the use of chemicals of the class defined above in which $R_1$ is methyl and $R_2$ is selected from the group consisting of phenyl, phenyl substituted with 1 or 2 methyl groups, monohalophenyl, and 2-naphthyl.

Preferred pyridine N-oxide derivatives employed as herbicides in accordance with the invention include
2-(2,5-dimethylphenylmethylsulfonyl)pyridine N-oxide,
2-(2,4,6-trimethylphenylmethylsulfonyl)pyridine N-oxide,
2-(2,6-dichlorophenylmethylsulfonyl)pyridine N-oxide,
2-(2,4-dichlorophenylmethylsulfinyl)pyridine N-oxide,
2-(2,6-dichlorophenylmethylsulfinyl)pyridine N-oxide,
2-(1-[4-methylphenyl]ethylsulfonyl)pyridine N-oxide,
2-(2,3,6-trichlorophenylmethylsulfonyl)pyridine N-oxide,
2-(2-methylphenylmethylsulfonyl)pyridine N-oxide,
2-(1-[4-fluorophenyl]ethylsulfonyl)pyridine N-oxide,
2-(1-[2,5-dimethylphenyl]ethylsulfonyl)pyridine N-oxide,
2-(2,3,6-trichlorophenylmethylsulfinyl)pyridine N-oxide,
2-(1-phenylethylsulfonyl)pyridine N-oxide,
2-(1-[2-napthyl]ethylsulfonyl)pyridine N-oxide,
2-[1-[4-chlorophenyl]ethylsulfonyl)-pyridine N-oxide,
2-(1-[4-bromophenyl]ethylsulfonyl)pyridine N-oxide,
2-(2,3,6-trimethylphenylmethylsulfonyl)pyridine N-oxide, and
2-(2,3,6-trimethylphenylmethylsulfinyl)pyridine N-oxide.

Particularly preferred are
2-(2,5-dimethylphenylmethylsulfonyl)pyridine N-oxide,
2-(2,6-dichlorophenylmethylsulfinyl)pyridine N-oxide,
2-(1-[2,5-dimethylphenyl]ethylsulfonyl)-pyridine N-oxide,
2-(2,4,6-trimethylphenylmethylsulfonyl)pyridine N-oxide,
2-(1-[2-naphthyl]ethylsulfonyl)pyridine N-oxide,
2-(1-[4-chlorophenyl]ethylsulfonyl)pyridine N-oxide,
2-(1-[4-methylphenyl]ethylsulfonyl)pyridine N-oxide, and
2-(2,3,6-trimethylphenylmethylsulfinyl)pyridine N-oxide.

The herbicidally effective pyridine N-oxide derivatives described herein are useful for both preemergence and postemergence control of weeds, and are furthermore remarkable for their ability to selectively control weeds without injury to desirable crops. Excellent control of weeds such as quackgrass [*Agropyron repens* (L.) Beauv.] fromm seed, Texas panicum (*Panicum texanum* Buckl.), giant foxtail (*Setaria faberi* Herrm.), yellow foxtail [*Setaria lutescens* (Weigel) Hubb.], green foxtail [*Setaria viridis* (L.) Beauv.], barnyardgrass [*Echinochloa crus-galli* (L.) Beauv.] and wild oats (*Avena fatua* L.) can be achieved with such chemicals as 2-(2,5-dimethylphenylmethylsulfonyl) pyridine N-oxide, without injury to such crops as flax (*Linum usitatissimum* L.), alfalfa (*Medicago sativa* L.), cotton (*Gossypium sp.*) soybeans [*Glycine max* (L.) Merr.] peanuts (*Arachis hypogaea* L.) tomatoes (*Lyloperison esculentum* Mill.) and tobacco (*Nicotiana tabacum* L.).

Surprisingly, the herein described 2-sulfinyl and 2-sulfonyl pyridine N-oxide herbicides are unexpectedly more effective than their corresponding sulfide precursors.

The procedures for using the present 2-sulfinyl and 2-sulfonyl pyridine N-oxide derivatives may be in accordance with conventional agricultural practice. The chemicals are ordinarily applied as formulations containing a carrier and/or surface-active agent. The formulation may contain more than one of the described pyridine N-oxide derivatives if desired; other active herbicides may be included in the formulation as well.

Thus, the chemical may be impregnated on finely divided or granular inorganic or organic carriers such as attapulgite clay, sand, vermiculite, corn cobs, activated carbon or other granular carriers known to the art. The impregnated granules may then be spread on the soil. Furthermore, the chemical may be formulated as a wettable powder by grinding it into a fine powder and mixing it with an inactive powdered carrier to which a surface active dispersing agent has been added. Typical powdered solid carriers are the various mineral silicates, e.g., mica, talc, pyrophyllite and clays. The wettable powder may then be dispersed in water and sprayed on the soil surface or weeds. Similarly, an emulsifiable concentrate may be prepared by dissolving the chemical in a solvent such as benzene, toluene, or other aliphatic or aromatic hydrocarbon to which a surface active dispersing agent has been added. The emulsifiable concentrate may then be dispersed in water and applied by spraying. Suitable surface active agents are well known to those skilled in the art and reference may be had to McCutcheon's Detergents and Emulsifiers, 1970, Allured Publishing Corp., Ridgewood, New Jersey; or Hoffman et al. U.S. Pat. Nos. 2,614,916, cols. 2 to 4 and 2,547,724, cols. 3 and 4, for example of appropriate surface active agents. The concentration of active chemical in the formulation may vary widely, e.g., from 1 to 95%. The concentration of active chemical in dispersions applied to the soil or foliage is almost invariably from 0.002% to 75%. The chemical is frequently applied at rates of 0.10 to 25 pounds per acre. For use as a preemergence herbicide, the chemical is applied to soil which contains weed and crop seed (either to the surface of the soil or incorporated into the upper one to three inches of soil).

The most suitable rate of application in any given case will depend on such factors as soil type, soil pH, soil organic matter content, the quantity and intensity of rainfall before and after treatment, the air and soil temperature, light intensity and light duration per day.

All of these factors can have an influence on the efficacy of the chemicals for use as herbicides.

The herbicidal use may include selective weed control in crops such as soybeans, cotton, flax and peanuts.

The 2-sulfinyl and 2-sulfonyl pyridine N-oxide derivatives employed as herbicides in this invention may be prepared from known compounds (see A. R. Katritsky, J. Chem. Soc., 191 [1957], U.S. Pat. Nos. 3,107,994 and 3,155,671 referred to above, and the E. Shaw et al. and W. Walter et al. articles referred to above). The parent 2-thiopyridine N-oxides are prepared by either of two procedures: (1) the reaction of 2-chloropyridine N-oxide with the appropriate mercaptan in the presence of an acid acceptor such as an alkaline earth hydroxide; (2) reaction of the sodium salt of 2-mercaptopyridine N-oxide with a suitable halide preferentially of the benzyl type but not limited to. The yields of the two procedures are comparable.

An alternate and useful synthetic route involves the oxidation of a 2-thiopyridine prepared by methods described in the literature. The oxidation involves the conversion of both the sulfur and nitrogen to their higher oxidative states in a single preparative step. In this case the products are sulfones as the sequence of oxidation proceeds from sulfide → sulfoxide → sulfone → sulfone N-oxide. The oxidant most generally employed, but not limited to, is 30 – 50% hydrogen peroxide in glacial acetic acid. In excess of three equivalents of peroxide is necessary.

The conversion of the 2-thiopyridine N-oxide to the analogous sulfinyl or sulfonyl compound is accomplished by employing one or two equivalents of an oxidizing agent selected from, but not necessarily limited to, hydrogen peroxide, peracetic acid, and the aromatic peroxy acids. The ratio of peroxide to substrate varies with the desired product. A general outline of routes and equivalents involved can be depicted as follows:

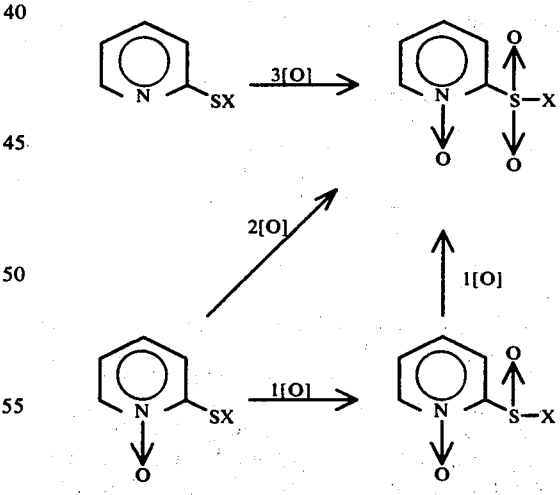

The solvents employed vary with the oxidant as described in the literature (Katritsky and Lagowski, Chemistry of the Heterocyclic N-Oxides, Academic Press, 1971). Glacial acetic acid and water are preferred when hydrogen peroxide is used and a nonpolar solvent such as chloroform with the aromatic peroxy acids. When water is employed as a solvent a catalyst of the nature of a tungsten, vanadium, zirconium or molybdenum salt (U.S. Pats. No. 3,005,852, Freyermuth et al., Oct. 24, 1961), U.S. Pat. No. 3006,962, Schultz et al., Oct. 31, 1961, U.S. Pat. No. 3,006,963, Buc et al., Oct. 31, 1961 and British Pat. No. 1,335,626, Eastman Kodak Co., Oct. 31, 1973) is generally used. Temperature and time are a function of the sulfide employed and with the range varying from 50° to reflux in the case of water and acetic acid to 0° to 40° with chloroform.

Compounds of the invention may be used for selective control of various grasses and broadleaved weeds including pigweed (*Amaranthus retroflexus* L.) and purslane (*Portulaca oleracea* L.) in diverse crops including flax (*Linumusitatissimum* L.), alfalfa (*Medicago sativa* L.), cotton (*Gossypium* sp.), soybeans [*Glycine max* (L.) Merr.], peanuts (*Arachis hypogaea* L.), tomatoes (*Lycopersicon esculentum* Mill.) and tobacco (*Nicotiana tabacum* L.). Application may be in acqueous solutions or suspensions which may be sprayed onto the soil surface prior to weed and crop emergence and before or after the crop seed is sown. The soil may receive a shallow tilling (less than 3 inches) after application of the chemical, but this is not required as it is with some preemergence herbicides. The compounds of this invention may also be applied by broadcast of a granular formulation prior to weed and crop emergence.

Various weeds such as crabgrass [*Digitaria ischaemum* (Schreb.) Muhl.] may be controlled by post-emergence application of compounds of this invention.

Compounds of this invention may be added as a "tank mix" to other herbicide solutions so that the number of different weed species controlled in a single application will be increased. The formulations of invention compounds may also include other herbicides so that the spectrum of weeds controlled by spray or granular application may be increased.

The following examples will serve to illustrate the practice of the invention in more detail. The examples summarized in Table I illustrate preparation of chemicals useful in the invention while subsequent examples illustrate control of weeds with the chemicals. In the examples the melting points are uncorrected. In Table I, the symbol IR in the Analysis column indicates that infrared data for the compound are given in Table II. The infrared data were obtained on a Perkin-Elmer Infracord (trademark). In the examples illustrating use of the chemicals, each chemical is identified by the example number assigned to the chemical in Table I.

EXAMPLE 1

2-(2,5-Dimethylphenylmethylsulfonyl)pyridine N-oxide.

To a stirred solution of 792 gms (2.2 mole) (40% aqueous solution) 2-mercaptopyridine N-oxide, sodium salt in 1400 ml of ethanol is added 344 gms (2.2 mole) 2,5-dimethylbenzylchloride over a period of 15 minutes. The mixture is brought to reflux for 15 minutes, filtered hot, and treated with 5 liters of cold water. The product is filtered off and oven dried to 533 gms of 2-(2, 5-dimethylphenylmethylthio)pyridine N-oxide. Yield 97%. Melting point 140° – 142° C.

A. To a vigorously stirred solution of 74 gms (0.3 mole) of the thio compound in 250 ml of glacial acetic acid at 45° – 50° C is added 75 ml of 30% hydrogen peroxide over a period of 15 minutes. The temperature is raised to 70° C and after 30 minutes increased again to 80° – 90° and held for 3 hours. The reaction mixture is lowered to ambient temperature and added slowly to two to 3 times its volume of vigorously agitated cold water. The pale yellow solid separates and is filtered off. Recrystallizes from ethanol to yield 74.5 gms of fine crystals melting at 156° – 158° C (IR N—O 1275 $cm^{-1}SO_2$ 1140, 1315 $cm^{-1}$). Yield 89% theory.

Analysis: Calc. for $C_{14}H_{15}NO_3S$. C 60.63; H 5.45; N 5.05; S 11.54. Found C 60.66; H 5.56; N 5.18; S 11.81.

B. To a heated (80° – 90°) vigorously stirred slurry of 30 gms (0.12 mole of thio compound in 150 ml of water containing 10 gms of acetic acid and 0.2 gms of sodium tungstate dihydrate is slowly added 26 ml of 30% hydrogen peroxide. The addition is exothermic and the temperature is maintained at 80° – 90° C for the first 14 ml then allowing it to rise to the 95° – 105° C range for the remaining 12 ml.

The initial slurry becomes quite thin at the sulfoxide stage and again separating at the sulfone stage. Overall reaction time is about one hour. The reaction mixture is filtered, washed with water and air dried. Melting point 156° – 158.° Mixed m.p. with authentic sample shows no depression. Yield 32.8 gms (quantitative).

EXAMPLE 2

2-(2,4,6-Trimethylphenylmethylsulfonyl)pyridine N-oxide.

A mixture of 17 gms (0.05 mole) 2-mercaptopyridine N-oxide, sodium salt (40% aqueous solution) and 8.5 gms (0.05 mole) $\alpha^2$ chloroisodurene in 50 ml of ethanol is brought to reflux for 15 minutes. The volatiles are removed and the residue extracted with 150 ml of boiling chloroform, filtered and dried over sodium sulfate. Evaporation and trituration of the residue with a few drops of acetone induce crystallization. A yield of 11.5 gms of 2-(2,4,6-trimethylphenylmethylthio)pyridine N-oxide is obtained. Melting point 137° – 138° C. Structure confirmed by IR and NMR.

To a well cooled (0° – 10° C) solution of 15 gms (0.06 mole) of thio compound in 200 ml of chloroform is slowly added with vigorous stirring 25 gms (0.12 mole) meta chloroperoxybenzoic acid (MCPBA) (85%) in 400 ml of chloroform. Upon completion of the addition the temperature is permitted to rise to ambient and stirring is continued 24 hours. The reaction mixture is washed thoroughly with 300 ml of saturated sodium bicarbonate solution and water then dried over magnesium sulfate. Evaporation of the chloroform, and crystallization of the solid residue from methanol yields 15 grams (86% theory) of product. Melting point 173° – 175° (IR N-O 1275 $cm^{-1}$, $SO_2$ 1310, 1140 $cm^{-1}$)

Analysis: Calc. for $C_{15}H_{17}NO_3S$. C 61.90; H 5.84; N 4.81. Found: C 61.97; H 6.06; N 4.79.

EXAMPLE 3

2-(2,6-Dichlorophenylmethylsulfinyl)-pyridine N-oxide

A mixture of 37 gms (0.1 mole) 2-mercaptopyridine N-oxide, sodium salt (40% aqueous solution) and 19.5 gms (0.1 mole) 2,6-dichlorobenzylchloride in 200 ml of ethanol is warmed to 65° – 70° for thirty minutes, cooled and filtered. The filter cake is washed thoroughly with water and finally with 40 ml of acetone. The dry cake (25.3 gms) represents a 92% yield of 2-(2,6-dichlorophenylmethylthio)pyridine N-oxide. Melting point 240° – 241° C. Structure confirmed by IR and NMR.

A solution of 5.8 gms (0.02 mole) of thio compound in 100 ml of chloroform is cooled to 0° – 10° C. Four (4) gms (0.02 mole) MCOBA (85%) is added with good stirring. After twenty four hours at ambient temperature the reaction mixture is washed thoroughly with sodium bicarbonate solution, dried and evaporated. Crystallization from hot ethyl acetate yielded 4.3 gms (71% theory) of product. Melting point 135° – 137° C (IR N-O 1260 cm$^{-1}$ SO 1050 cm$^{-1}$).

Analysis: Calc. for $C_{12}H_9Cl_2NO_2S$. C 47.65; H 2.98; N 4.64. Found C 47.25; H 2.95; N 4.29.

EXAMPLE 4

2-(1-[4-Chlorophenyl]ethylsulfonyl)-pyridine N-oxide

The intermediate 2-(1-[4-chlorophenyl]ethylthio)-pyridine N-oxide is prepared from 1-(4-chlorophenyl)ethylchloride and 2-mercaptopyridine N-oxide, sodium salt by the procedure described in Example 2. Melting point 106° – 108° C. Structure confirmed by IR and NMR.

The thio compound (0.02 mole) is oxidized with MCPBA (0.04 mole) and isolated in the manner previously described in Example 2. Yield 78% theory. Melting point 188° – 191° C (IR N-O 1300 cm$^{-1}$ SO$_2$ 1340, 1160 cm$^{-1}$).

Analysis: Calc. for $C_{13}H_{12}ClNO_3S$. C 52.44; H 4.06; N 4.71. Found: C 52.09; H 4.11; N 4.61.

EXAMPLE 5

2-(1-[4-Methylphenyl]ethylsulfonyl)-pyridine N-oxide

The intermediate compound 2-(1-[4-methylphenyl]ethylthiol)pyridine N-oxide is prepared from 1-(4-methylphenyl)ethyl chloride and 2-mercaptopyridine N-oxide, sodium salt by the procedure described in Example 2. Melting point 83° – 85° C. Structure confirmed by IR and NMR.

The thio compound (0.02 mole) is oxidized with MCPBA (0.04 mole) and isolated in the manner described in Example 2. (IR N-O 1275 cm$^{-1}$ SO$_2$ 1315, 1140 cm$^{-1}$)

Analysis: Calc. for $C_{14}H_{15}NO_3S$. C 60.35; H 5.45; N 5.02. Found C 61.18; H 5.70; N 5.22.

EXAMPLE 6

2-(1-[2,5-Dimetylphenyl]ethylsulfonyl)pyridine N-oxide

The intermediate 2-(1-[2,5-dimethylphenyl]ethylthio)pyridine N-oxide is prepared from 1-(2,5-dimethylphenyl)ethyl chloride and 2-mercaptopyridine N-oxide, sodium salt by the procedure described in Example 2. Melting point 118° – 120° C. Structure confirmed by IR and NMR.

The thio compound (0.05 mole) is oxidized with MCPBA (0.1 mole) and isolated in the manner described in Example 2. Yield 83% theory. Melting point 160° – 163° C. (IR N-O 1275 cm$^{-1}$, SO$_2$ 1315, 1145 cm$^{-1}$)

EXAMPLE 7

2-(1-[2-Naphthyl]ethylsulfonyl)pyridine N-oxide

The intermediate 2-(1-[2-naphthyl]ethylthio)pyridine N-oxide is prepared from 1-(2-naphthyl)ethyl chloride and 2-mercapto pyridine N-oxide, sodium salt by the procedure described in Example 2. Melting point 112° – 115° C. Structure confirmed by IR and NMR.

The thio compound (0.02 mole) is oxidized with MCPBA (0.04 mole) and isolated in the manner described in Example 2. Crystallization from ethanol yielded 73% product. Melting point 144° – 146° C. (IR N-O 1275 cm$^{-1}$, SO$_2$ 1310, 1140 cm$^{-1}$)

EXAMPLE 8

2-(2,3,6-Trimethylphenylmethylsulfinyl)-pyridine N-oxide

The intermediate 2-(2,3,6-trimethylphenylmethylthio)pyridine N-oxide is prepared from $\alpha^2$-bromoprehnitene with 2-mercaptopyridine N-oxide, sodium salt by the procedure described in Example 2. Yield 50% theory. Melting point 108° – 110° C. Structure confirmed by IR and NMR.

The thio compound (0.03 mole) is oxidized with MCPBA (0.03 mole) and isolated in the manner described in Example 2. Yield 50% theory. Melting point 72° – 75° C. (IR N-O 1250 cm$^{-1}$, SO 1050 cm$^{-1}$)

EXAMPLE 9

2-(1-Phenylethylsulfonyl)pyridine N-oxide

To a well stirred, cold (0° – 10°) solution of 46.3 gms (0.2 mole) of 2-(1-phenylethylthio)pyridine N-oxide in 400 ml of chloroform is slowly added a solution of 80 gms (0.4 mole) MCPBA in one liter of chloroform. After three hours at 0° – 10° the temperature was allowed to become ambient and stand for twenty-four hours. After washing with saturated sodium bicarbonate to remove all traces of acid the chloroform solution was dried and evaporated. Yield 47 gms (90% theory). Melting point 141° – 143° C. (IR N-O 1260 cm$^{-1}$, SO$_2$ 1300, 1140 cm$^{-1}$)

Analysis: Calc. for $C_{13}H_{13}NO_3S$. C 59.40; H 4.95; N 5.32. Found C 59.03; H 4.90; N 5.35.

EXAMPLE 10

2-(2,4-Dichlorophenylmethylsulfinyl)-pyridine N-oxide

A well stirred solution of 5.8 gms (0.02 mole) of 2-(2,4-dichlorophenylmethylthio)pyridine N-oxide in 50 ml of chloroform is treated at 0° – 10° with 4 gms (0.02 mole) MCPBA (85%) in 50 ml of chloroform. The mixture is allowed to rise to ambient and held for 16 hours. The reaction mixture is washed with saturated sodium bicarbonate, dried and evaporated to 5.5 gms (89% theory) of product. Melting point 138° – 141° C. Structure confirmed by IR and NMR. (IR N-O 1240 cm$^{-1}$, SO 1050 cm$^{-1}$)

EXAMPLE 11

2-(2-Methylphenylmethylsulfonyl)pyridine N-oxide

The intermediate 2-(2-methylphenylmethylthio)pyridine N-oxide is prepared by the procedure described in Example 2 from $\alpha$-chloro o-xylene and 2-mercaptopyridine N-oxide sodium salt. Melting point 134° –136° C. Yield 85% theory. Structure confirmed by IR and NMR.

A slurry of 14 gms (0.06 mole) thio compound, 100 ml water, 0.5 gms sodium tungstate dihydrate, and 4 ml of glacial acetic acid is heated to 75° C. Twelve (12) ml hydrogen peroxide (30%) (0.12 mole) is added portionwise and with only a slight exotherm until 6 ml is consumed. The remaining 6 ml is added at steam bath temperature in three (3) 2 ml portions at a rate controlled by testing the mixture with potassium iodidestarch paper to assure consumption of the previous peroxide. The final temperature was 97° after one hour. Cool, filter and wash cake with water and a small amount of cold ethanol. After drying the product 15.4 gms (99% theory) is obtained. Melting point 159° – 160.5° C. Structure confirmed by IR.

Analysis: Calc. for $C_{13}H_{13}NO_3S$. C 59.31; H 4.98; N 5.32. Found: C 59.30; H 5.21; N 5.31.

EXAMPLE 12

2-(2,2-Dichloro-1-methylcyclopropylmethylsulfonyl)-pyridine N-oxide

To a well stirred solution of 62.5 gms (0.25 mole) 2-(2,2-dichloro-1-methylcyclopropylmethylthio)pyridine in 250 ml of glacial acetic acid at ambient temperature 90 gms (0.8 mole) of 30% hydrogen peroxide is slowly added. The temperature is increased to 80° over a period of two hours and held for 12 hours. An additional 10 ml of peroxide is added and heating continued for 4 hours.

The reaction mixture was reduced to approximately one-third its volume with a rotary evaporator and the residue slowly poured into a vigorously stirred four fold volume of cold water. The separated product is filtered off and vacuum dried to 31.5 gms. Yield 42% theory. Melting point 93° – 94° C (IR N-O 1280 cm$^{-1}$, SO$_2$ 1315, 1140 cm$^{-1}$)

Analysis: Calc. for $C_{10}H_{11}Cl_2NO_3S$. C 40.50; H 3.72; Cl 23.95; N 4.72. Found: C 40.36; H 3.77; Cl 24.15; N 4.63.

EXAMPLE 13

2-(2,3,6-Trichlorophenylmethylsulfinyl)pyridine N-oxide

The intermediate 2-(2,3,6-trichlorophenylmethylthio)pyridine N-oxide is prepared from 2,3,6-trichlorobenzylchloride and 2-mercaptopyridine N-oxide sodium salt by the procedure employed in Example 3. Melting point 232° – 234° C. Yield quantitative. Structure confirmed by IR and NMR.

A slurry of 6.4 gms (0.02 mole) of thio compound in 50 ml of chloroform is cooled to 5° – 10° C and solution of 4 gms (0.02 mole) MCPBA in 100 ml of chloroform is slowly added. The reaction mixture is allowed to rise to room temperature, stirred for 16 hours, washed with saturated sodium bicarbonate solution and dried over sodium sulfate. The dry solution is evaporated to dryness and crude product refluxed in ethanol, cooled and filtered. Yield of product 65% theory. Melting point 168° – 170° C. (IR N-O 1350 cm$^{-1}$, SO 1050 cm$^{-1}$)

Analysis: Calc. for $C_{12}H_8Cl_3NO_2S$. C 42.82; H 2.39; N 4.16; S 9.54. Found: C 41.01; H 2.32; N 4.18; S 9.74.

EXAMPLE 14

2-(2,6-Dichlorophenylmethylsulfonyl)pyridine N-oxide

A mixture of 37 gms (0.1 mole) of (40% solution) 2-mercaptopyridine N-oxide, sodium salt and 19.5 gms (0.1 mole) 2,6-dichlorobenzylchloride in 200 ml ethanol is warmed to 65° for thirty minutes, cooled and filtered. The filter cake is washed thoroughly with water and finally with 40 ml of acetone. Vacuum drying of the cake yields 25.3 gms (92% theory) of product, 2-(2,6-dichlorophenylmethylthio)pyridine N-oxide. Melting point 240° – 241° C. Structure confirmed by IR.

A slurry of 29 gms (0.1 mole) of the thio compound in 300 ml of chloroform at 10° is treated slowly with 40 gms (0.2 mole) MCPBA (85%) in 450 ml of chloroform. The mixture is permitted to rise to ambient temperature resulting in a clear solution which is held sixteen hours. The solution is washed with saturated sodium bicarbonate solution, dried over magnesium sulfate and evaporated to dryness. The residue is slurried in 400 ml of boiling methanol, cooled and filtered to yield 28 gms (89% theory) of product. Melting point 214° – 215.5° C.

Analysis: Calc. for $C_{12}H_9Cl_2NO_3S$. C 45.32; H 2.83; N 4.40. Found: C 45.67; H 2.89; N 4.55.

EXAMPLE 15

2-(2,3,6-Trichlorophenylmethylsulfonyl)pyridine N-oxide

The compound 2-(2,3,6-trichlorophenylmethylthio)pyridine N-oxide is prepared from 2,3,6-trichlorobenzylchloride and 2-mercaptopyridine N-oxide sodium salt by the procedure employed in Example 1. Melting point 232° – 234° C. Yield quantitative. Structure confirmed by IR and NMR.

A slurry of 6.4 gms (0.02 mole) of thio compound in 50 ml of chloroform is cooled to 5° – 10° C and a solution of 8 gms (0.04 mole) MCPBA in 100 ml of chloroform is slowly added. The reaction mixture is allowed to rise to room temperature, stirred for 16 hours, washed with saturated sodium bicarbonate solution and dried over sodium sulfate. The dry solution is evaporated to dryness and crude product refluxed in ethanol, cooled and filtered. Yield of product 6.7 gms (95% theory). Melting point 194° – 196° C. Structure confirmed by IR and NMR.

EXAMPLE 16

2-(1-[4-Fluorophenyl]ethylsulfonyl)pyridine N-oxide

The compound is prepared from 2-mercaptopyridine N-oxide sodium salt and 1-(4-fluorophenyl)ethylchloride in the manner described in example 4. The 2-(1-[4-fluorophenyl]ethylthio)pyridine N-oxide is obtained in 40% yield. Melting point 95° – 97° C. Structure confirmed by IR and NMR.

Oxidation of the thio compound (0.04 mole) with 0.08 mole) MCPBA and isolation procedure are the same as employed in example 7. Yield 83%. Melting point 142° – 144° C.

Analysis: Calc. for $C_{13}H_{12}FNO_3S$. C 55.50; H 4.30; N 4.98. Found: C 55.47; H 4.61; N 5.07.

EXAMPLE 17

2-(1-[4-Bromophenyl]ethylsulfonyl)pyridine N-oxide

The compound 2-(1-[4-bromophenyl]ethylthio)pyridine N-oxide is prepared from 1-(4-bromophenyl)ethylchloride and 2-mercaptopyridine N-oxide sodium salt by the procedure described in Example 1. The melting point is 113° – 115° C. Structure is confirmed by IR and NMR.

The thio compound (0.05 mole) is oxidized with MCPBA (0.1 mole) and isolated in the manner previously described in Example 9. Yield 85%. Structure confirmed by IR and NMR.

Analysis: Calc. for $C_{13}H_{12}BrNO_3S$. C 45.63; H 3.45; N 4.09. Found: C 45.04; H 3.32; N 4.15.

In accordance with the same procedure the chemicals listed in Table I may be prepared. Table I summarizes the foregoing preparations as well as additional similar preparations; Table II gives infrared data. The numbers assigned to the preparations in Table I are used to identify the chemicals in the subsequent examples. Compound 44 in Table I also contained a minor amount of the 4-ethylphenyl isomer.

Table I

| | | Herbicidal Chemicals | | Analysis-Calc/Found | | | |
|---|---|---|---|---|---|---|---|
| Ex. | Name | m.p. | C | H | N | S |
| 12 | 2-(2,2-Dichloro-1-methylcyclopropylmethylsulfonyl)pyridine N-oxide | 93–95° | 40.50 / 40.51 | 3.72 / 3.87 | 4.73 / 4.59 | 10.81 / 10.94 |
| 38 | 2-(2,2-Dichlorocyclopropylmethylsulfonyl)pyridine N-oxide | 103–105 | | IR | | |
| 24 | 2-(1-Naphthylmethylsulfonyl)pyridine N-oxide | 183–186 | | IR | | |
| 20 | 2-(Phenylmethylsulfonyl)pyridine N-oxide | 126–128 | | IR | | |
| 21 | 2-(3,4-Dimethylphenylmethylsulfonyl)pyridine N-oxide | 165–167 | 60.63 / 60.77 | 5.45 / 5.73 | 5.05 / 5.03 | 11.54 / 11.71 |
| 22 | 2-(4-Methylphenylmethylsulfonyl)pyridine N-oxide | 149–151 | | IR | | |
| 23 | 2-(4-Chlorophenylmethylsulfonyl)pyridine N-oxide | 154–155 | | IR | | |
| 1 | 2-(2,5-Dimethylphenylmethylsulfonyl)pyridine N-oxide | 156–158 | 60.63 / 60.66 | 5.45 / 5.56 | 5.05 / 5.18 | 11.54 / 11.81 |
| 26 | 2-(4-Nitrophenylmethylsulfonyl)pyridine N-oxide | 215–215 | | IR | | |
| 11 | 2-(2-Methylphenylmethylsulfonyl)pyridine N-oxide | 159–161 | 59.31 / 59.30 | 4.93 / 5.21 | 5.32 / 5.31 | |
| 14 | 2-(2,6-Dichlorophenylmethylsulfonyl)pyridine N-oxide | 214–216 | 45.37 / 45.67 | 2.83 / 2.89 | 4.40 / 4.55 | |
| 2 | 2-(2,4,6-Trimethylphenylmethylsulfonyl)pyridine N-oxide | 173–175 | 61.90 / 61.97 | 5.84 / 5.06 | 4.81 / 4.79 | |
| 33 | 2-([3-trifluoromethylphenyl]methylsulfonyl)pyridine N-oxide | 125–127 | 49.10 / 48.86 | 3.16 / 2.73 | 4.41 / 4.20 | |
| 34 | 2-(2,4-Dichlorophenylmethylsulfonyl)pyridine N-oxide | 154–156° | | IR | | |
| 9 | 2-(1-Phenylethylsulfonyl)pyridine N-oxide | 141–143 | 59.40 / 59.03 | 4.95 / 4.90 | 5.32 / 5.35 | |
| 35 | 2-(4-Methoxyphenylmethylsulfonyl)pyridine N-oxide | 131–133 | | IR | | |
| 31 | 2-(2-Chlorophenylmethylsulfonyl)pyridine N-oxide | 151–152 | | IR | | |
| 37 | 2-(Diphenylmethylsulfonyl)pyridine N-oxide | 204–205 | 66.40 / 66.26 | 4.61 / 4.71 | 4.31 / 4.40 | |
| 36 | 2-([2-Methoxy-5-nitrophenyl]methylsulfonyl)pyridine N-oxide | 226–227 | | IR | | |
| 42 | 2-(2-Fluorophenylmethylsulfonyl)pyridine N-oxide | 151–153 | 54.00 / 54.03 | 3.74 / 3.79 | 5.24 / 5.31 | |
| 41 | 2-[(3,4-Dioxymethylene-6-chlorophenyl)methylsulfonyl]pyridine N-oxide | 179–180 | 47.60 / 46.87 | 3.06 / 2.83 | 4.28 / 4.23 | |
| 44 | 2-(2-Ethylphenylmethylsulfonyl)pyridine N-oxide | — | | IR | | |
| 55 | 2-(3-Methylphenylmethylsulfonyl)pyridine N-oxide | 171–173 | | IR | | |
| 48 | 2-(2-Cyanophenylmethylsulfonyl)pyridine N-oxide | 188–190 | 56.90 / 57.14 | 3.65 / 3.98 | 10.21 / 10.22 | |
| 62 | 2-(3-Fluorophenylmethylsulfonyl)pyridine N-oxide | 138–140 | | IR | | |
| 64 | 2-(4-Fluorophenylmethylsulfonyl)pyridine N-oxide | 136–138 | | IR | | |
| 40 | 2-(Cinnamylthio)pyridine N-oxide | 122–124 | 61.00 / 60.32 | 4.72 / 4.57 | 5.09 / 5.03 | |
| 4 | 2[1-(4-Chlorophenyl)ethylsulfonyl]pyridine N-oxide | 188–191 | | IR | | |
| 38 | 2-(Isopropenylmethylsulfonyl)pyridine N-oxide | oil | | IR | | |
| 39 | 2-(Phenylethylsulfonyl)pyridine N-oxide | 99–100 | | IR | | |
| 43 | 2-(1-Ethylpentylsulfonyl)pyridine N-oxide | oil | | IR | | |
| 45 | 2-(Cyclohexylsulfonyl)pyridine N-oxide | 135–138 | | IR | | |
| 49 | 2-(2-Propylsulfonyl)pyridine N-oxide | 110–114 | 47.75 / 47.86 | 5.51 / 5.57 | 6.96 / 6.78 | |
| 47 | 2-(Cycloheptylsulfonyl)pyridine N-oxide | 103–107 | 56.50 / 57.14 | 6.66 / 6.80 | 5.50 / 5.55 | |
| 3 | 2-(2,6-Dichlorophenylmethylsulfinyl)pyridine N-oxide | 135–137° | 47.65 / 47.25 | 2.98 / 2.95 | 4.64 / 4.25 | |
| 46 | 2-(2-5-Dimethylphenylmethylsulfinyl)pyridine N-oxide | 142–144 | 64.80 / 64.43 | 5.64 / 5.67 | 5.26 / 5.13 | |
| 54 | 2-(3-Methylphenylmethylsulfinyl)pyridine N-oxide | 67–71 | 63.20 / 63.14 | 5.26 / 5.71 | 5.66 / 5.73 | |
| 10 | 2-(2,4-Dichlorophenylmethylsulfinyl)pyridine N-oxide | 138–141 | | IR | | |
| 52 | 2-(4-Methoxyphenylmethylsulfinyl)pyridine N-oxide | 140–143 | | IR | | |
| 53 | 2-(Phenylmethylsulfinyl)pyridine N-oxide | 119–122 | | IR | | |
| 51 | 2-[(3-Trifluoromethylphenyl)methylfulfinyl]pyridine | 104–108 | 51.80 / 52.13 | 3.34 / 3.35 | 4.65 / 4.75 | |
| 56 | 2-(2,4,6-Trimethylphenylmethylsulfinyl)pyridine N-oxide | 164–166° | 65.50 / 66.11 | 6.18 / 6.49 | 5.09 / 5.15 | |
| 57 | 2-(2-Chlorophenylmethylsulfinyl)pyridine N-oxide | 124–127 | 53.65 / 53.91 | 3.73 / 4.11 | 5.22 / 5.25 | |
| 58 | 2-(3,4-Dimethylphenylmethylsulfinyl)pyridine N-oxide | 123–126 | 64.43 / 64.89 | 5.75 / 6.08 | 5.36 / 5.40 | |
| 59 | 2-(2-Methylphenylmethylsulfinyl)pyridine N-oxide | 99–102 | 63.14 / 62.66 | 5.30 / 5.31 | 5.66 / 5.45 | 12.96 / 12.57 |
| 60 | 2-(2-Cyanophenylmethylsulfinyl)pyridine N-oxide | 158–161 | 60.45 / 60.03 | 3.90 / 3.86 | 10.84 / 10.57 | |
| 61 | 2-(4-Methylphenylmethylsulfinyl)pyridine N-oxide | 101–103 | 63.14 / 63.57 | 5.30 / 5.43 | 5.66 / 5.48 | 12.96 / 13.29 |
| 63 | 2-(4-Fluorophenylmethylsulfinyl)pyridine N-oxide | 100–103 | | IR | | |
| 65 | 2-(3-Fluorophenylmethylsulfinyl)pyridine N-oxide | 70–74 | | IR | | |
| 29 | 2-Ethylsulfinyl pyridine N-oxide | 94–96° | | IR | | |
| 32 | 2-Cyanomethylsulfinyl pyridine N-oxide | 164–165 | | IR | | |
| 66 | 2-(2-Fluorophenylmethylsulfinyl)pyridine N-oxide | 110–113 | 57.40 / 57.43 | 3.98 / 3.95 | 5.57 / 5.68 | |
| 67 | 2-(Diphenylmethylsulfinyl)pyridine N-oxide | 188–191 | | IR | | |
| 27 | 2-(Cyclohexylmethylsulfonyl)pyridine N-oxide | 144–145° | | IR | | |
| 68 | 2-(2-Methoxy-5-methylphenylmethylsulfonyl)pyridine N-oxide | 115–118 | | IR | | |

Table I-continued

Herbicidal Chemicals

| Ex. | Name | m.p. | C | H | N | S |
|---|---|---|---|---|---|---|
| 69 | 2-(2-Bromo-5-methoxyphenylmethylsulfonyl)pyridine N-oxide | 157–158 | | | IR | |
| 70 | 2-(Pentachlorophenylmethylsulfonyl)pyridine N-oxide | 235–238 | | | IR | |
| 15 | 2-(2,3,6-Trichlorophenylmethylsulfonyl)pyridine N-oxide | 194–196 | | | IR | |
| 72 | 2-(4-Cyanophenylmethylsulfonyl)pyridine N-oxide | 215–217 | | | IR | |
| 30 | 2-(2-Benzothiazolylmethylsulfonyl)pyridine N-oxide | 175–176 | 50.95 / 49.9 | 3.27 / 3.54 | 9.15 / 11.03 | 20.9 / 18.85 |
| 7 | 2-[1-(2-Naphthyl)ethylsulfonyl]pyridine N-oxide | 144–146 | | | IR | |
| 74 | 2-(2,5-Diisopropylphenylmethylsulfonyl)pyridine N-oxide | 120–123 | 64.84 / 64.10 | 6.95 / 6.89 | 4.20 / 4.31 | |
| 76 | 2-(1-Phenylbutylsulfonyl)pyridine N-oxide | 145–148 | 61.83 / 61.53 | 5.88 / 5.85 | 5.05 / 4.95 | |
| 5 | 2-[1-(4-Methylphenyl)ethylsulfonyl]pyridine N-oxide | 158–160 | 60.35 / 61.18 | 5.45 / 5.70 | 5.05 / 5.22 | |
| 78 | 2-[1-(2-Thienyl)ethylsulfonyl]pyridine N-oxide | 147–149 | 49.05 / 48.90 | 4.12 / 4.39 | 5.20 / 5.21 | |
| 16 | 2-[1-(4-Fluorophenyl)ethylsulfonyl]pyridine N-oxide | 142–144 | 55.50 / 55.47 | 4.30 / 4.61 | 4.98 / 5.07 | |
| 6 | 2-[1-(2,5-Dimethylphenyl)ethylsulfonyl]pyridine N-oxide | 160–163 | | | IR | |
| 17 | 2-[1-(4-Bromophenyl)ethylsulfonyl]pyridine N-oxide | 193–195° | 45.63 / 45.04 | 3.45 / 3.32 | 4.09 / 4.15 | |
| 81 | 2-(1-Phenylpropylsulfonyl)pyridine N-oxide | 144–146 | 60.63 / 60.57 | 5.45 / 5.39 | 5.05 / 5.11 | |
| 82 | 2-(3,4-Dichlorophenylmethylsulfonyl)pyridine N-oxide | 170–173 | 45.30 / 45.20 | 2.85 / 2.41 | 4.40 / 4.49 | |
| 25 | 2-(4-Chlorophenylmethylsulfinyl)pyridine N-oxide | 104–107 | | | IR | |
| 71 | 2-(Pentachlorophenylmethylsulfinyl)pyridine N-oxide | 213–215 | | | IR | |
| 13 | 2-(2,3,6-Trichlorophenylmethylsulfinyl)pyridine N-oxide | 168–170 | | | IR | |
| 73 | 2-(4-Cyanophenylmethylsulfinyl)pyridine N-oxide | 155–158 | | | IR | |
| 79 | 2-[1-(4-Fluorophenyl)ethylsulfinyl]pyridine N-oxide | 98–101 | 58.85 / 54.94 | 4.56 / 5.08 | 5.28 / 5.34 | |
| 75 | 2-(2,5-Diisopropylphenylmethylsulfinyl)pyridine N-oxide | 83–86 | | | IR | |
| 77 | 2-[1-(4-Methylphenyl)ethylsulfinyl]pyridine N-oxide | 121–123 | | | IR | |
| 19 | 2-(2,2-Dichlorocyclopropylmethylsulfinyl)pyridine N-oxide | oil | | | IR | |
| 50 | 2-(Phenylethylsulfinyl)pyridine N-oxide | oil | | | IR | |
| 80 | 2-[1-(4-Bromophenyl)ethylsulfinyl]pyridine N-oxide | 177–180 | | | IR | |
| 83 | 2-(3,4-Dichlorophenylmethylsulfinyl)pyridine N-oxide | 133–135 | 47.70 / 47.44 | 3.00 / 2.92 | 4.64 / 4.71 | |
| 84 | 2-(3-Bromophenylmethylsulfonyl)pyridine N-oxide | 145–147° | | | IR | |
| 86 | 2-(1-[3,4-Dichlorophenyl]ethylsulfonyl)pyridine N-oxide | 129–134 | | | IR | |
| 88 | 2-(3,4-Methylenedioxyphenylmethylsulfonyl)pyridine N-oxide | 163–165 | | | IR | |
| 91 | 2-(α-[4-Chlorophenyl]phenylmethylsulfonyl)pyridine N-oxide | 165–168 | | | IR | |
| 18 | 2-(2,3,6-Trimethylphenylmethylsulfonyl)pyridine N-oxide | 155 | | | IR | |
| 85 | 2-(3-Bromophenylmethylsulfinyl)pyridine N-oxide | 115–117 | | | IR | |
| 87 | 2-(3,4-Methylenedioxyphenylmethylsulfinyl)pyridine N-oxide | 171–173 | | | IR | |
| 89 | 2-(2-Pyridylmethylsulfinyl)pyridine N-oxide | 128–131 | | | IR | |
| 90 | 2-(α-[4-Chlorophenyl]phenylmethylsulfinyl)pyridine N-oxide | 109–114 | | | IR | |
| 94 | 2-(2-Nitrophenylmethylsulfonyl)pyridine N-oxide | 165–167 | | | IR | |
| 8 | 2-(2,3,6-Trimethylphenylmethylsulfinyl)pyridine N-oxide | 72–75 | | | IR | |
| 96 | 2-(Methyl-1-naphthylmethylsulfinyl)pyridine N-oxide | 127–130 | | | IR | |
| 98 | 2-(2-Iodophenylmethylsulfinyl)pyridine N-oxide | 160–163 | | | IR | |
| 101 | 2-(4-[2,2-Dichlorocyclopropyl]phenylmethylsulfinyl)-pyridine N-oxide | oil | | | IR | |
| 103 | 2-(1-[1-Naphthyl]ethylsulfinyl)pyridine N-oxide | 146–147 | | | IR | |
| 93 | 2-(2-Nitrophenylmethylsulfonyl)pyridine N-oxide | 155–158 | | | IR | |
| 92 | 2-(1-[2,4,6-Trimethylphenyl]ethylsulfonyl)pyridine N-oxide | 172–175 | | | IR | |
| 95 | 2-(Methyl-1-naphthylmethylsulfonyl)pyridine N-oxide | 195–198 | | | IR | |
| 97 | 2-(2-Iodophenylmethylsulfonyl)pyridine N-oxide | 142–146 | | | IR | |
| 99 | 2-(1-[4-Nitrophenyl]ethylsulfonyl)pyridine N-oxide | 167–121 | | | IR | |
| 100 | 2-(4-[2,2-Dichlorocyclopropyl]phenylmethylsulfonyl)pyridine N-oxide | oil | | | IR | |
| 104 | 2-(α-[2-Methylphenyl]phenylmethylsulfonyl)pyridine N-oxide | 122–125 | 67.24 / 66.52 | 5.05 / 5.29 | 4.13 / 4.13 | |
| 102 | 2-(1-[1-Naphthyl]ethylsulfonyl)pyridine N-oxide | wax | | | IR. | |
| 105 | 2-(1-[4-Methylsulfonylphenyl]ethylsulfonyl)pyridine N-oxide | 237–239 | | | IR | |
| 106 | 2-(1-[4-Methylsulfonylphenyl]ethylsulfinyl)pyridine N-oxide | 149–150 | | | IR | |
| 107 | 2-(3,4-Dimethoxyphenylmethylsulfinyl)pyridine N-oxide | 133–135 | | | IR | |
| 108 | 2-(3,4-Dimethoxyphenylmethylsulfonyl)pyridine N-oxide | 159–161 | | | IR | |
| 109 | 2-(1-[2,5-Diethylphenyl]ethylsulfonyl)pyridine N-oxide | 124–127 | | | IR | |
| 110 | 2-(Cyclopentylsulfonyl)pyridine N-oxide | 107–109 | | | IR | |
| 111 | 2-(2,5-Dimethoxyphenylmethylsulfonyl)pyridine N-oxide | 129–132 | | | IR | |
| 112 | 2-(2,5-Dimethoxyphenylmethylsulfinyl)pyridine N-oxide | 136–138 | | | IR | |
| 113 | 2-(2-Ethoxyphenylmethylsulfinyl)pyridine N-oxide | 135–138 | | | IR | |
| 114 | 2-(2-Ethoxyphenylmethylsulfonyl)pyridine N-oxide | 145–147 | | | IR | |

Table II

Infrared Data

| Ex | $SO_n$ | n | N-oxide |
|---|---|---|---|
| 12 | 1315, 1140 | 2 | 1280, 844 |
| 28 | 1320, 1145 | 2 | 1280, 845 |
| 24 | 1320, 1155 | 2 | 1280, 845 |
| 20 | 1320, 1150 | 2 | 1280, 840 |
| 21 | 1310, 1140 | 2 | 1270, 840 |
| 22 | 1320, 1140 | 2 | 1275, 840 |
| 23 | 1320, 1145 | 2 | 1280, 840 |
| 1 | 1310, 1130 | 2 | 1270, 835 |
| 26 | 1320, 1150 | 2 | 1280, 845 |
| 11 | 1310, 1130 | 2 | 1270, 840 |
| 14 | 1320, 1120 | 2 | 1240, 840 |
| 2 | 1310, 1140 | 2 | 1275, 840 |
| 33 | 1320, 1155 | 2 | 1280, 840 |
| 34 | 1310, 1140 | 2 | 1280, 840 |

Table II-continued

Infrared Data — Major Bands (cm$^{-1}$)

| Ex | SO$_n$ | n | N-oxide |
|---|---|---|---|
| 9 | 1300, 1140 | 2 | 1260, 840 |
| 35 | 1310, 1150 | 2 | 1250, 840 |
| 31 | 1320, 1160 | 2 | 1275, 835 |
| 37 | 1320, 1140 | 2 | 1280, 845 |
| 36 | 1320, 1140 | 2 | 1275, 835 |
| 42 | 1310, 1120 | 2 | 1270, 840 |
| 41 | 1320, 1140 | 2 | 1280, 840 |
| 44 | 1320, 1150 | 2 | 1270, 840 |
| 55 | 1320, 1120 | 2 | 1280, 845 |
| 48 | 1320, 1150 | 2 | 1280, 850 |
| 62 | 1330, 1130 | 2 | 1290, 845 |
| 64 | 1340, 1160 | 2 | 1290, 855 |
| 4 | 1340, 1160 | 2 | 1300, 850 |
| 38 | 1320, 1120 | 2 | 1275, 840 |
| 39 | 1310, 1125 | 2 | 1270, 840 |
| 43 | 1310, 1140 | 2 | 1280, 845 |
| 45 | 1310, 1130 | 2 | 1250, 840 |
| 49 | 1310, 1150 | 2 | 1240, 850 |
| 47 | 1300, 1140 | 2 | 1270, 840 |
| 3 | 1050 | 1 | 1260, 840 |
| 46 | 1055 | 1 | 1260, 830 |
| 54 | 1040 | 1 | 1250, 835 |
| 10 | 1050 | 1 | 1240, 840 |
| 52 | 1040 | 1 | 1250, 835 |
| 53 | 1050 | 1 | 1240, 835 |
| 51 | 1060 | 1 | 1250, 840 |
| 56 | 1050 | 1 | 1255, 840 |
| 57 | 1050 | 1 | 1260, 845 |
| 58 | 1055 | 1 | 1260, 840 |
| 59 | 1060 | 1 | 1260, 845 |
| 60 | 1055 | 1 | 1260, 840 |
| 61 | 1050 | 1 | 1260, 840 |
| 63 | 1060 | 1 | 1260, 845 |
| 65 | 1050 | 1 | 1260, 840 |
| 29 | 1040 | 1 | 1240, 830 |
| 32 | 1050 | 1 | 1240, 845 |
| 66 | 1065 | 1 | 1270, 850 |
| 67 | 1065 | 1 | 1270, 845 |
| 27 | 1300, 1130 | 2 | 1285, 840 |
| 68 | 1310, 1140 | 2 | 1260, 840 |
| 69 | 1320, 1140 | 2 | 1260, 845 |
| 70 | 1330, 1130 | 2 | 1280, 850 |
| 15 | 1325, 1125 | 2 | 1240, 850 |
| 72 | 1310, 1140 | 2 | 1280, 850 |
| 30 | 1330, 1155 | 2 | 1280, 840 |
| 7 | 1310, 1140 | 2 | 1275, 855 |
| 74 | 1320, 1140 | 2 | 1275, 845 |
| 76 | 1320, 1145 | 2 | 1280, 850 |
| 5 | 1315, 1140 | 2 | 1275, 845 |
| 78 | 1320, 1155 | 2 | 1280, 850 |
| 16 | 1310, 1140 | 2 | 1280, 840 |
| 6 | 1315, 1145 | 2 | 1275, 845 |
| 17 | 1310, 1140 | 2 | 1275, 845 |
| 81 | 1320, 1150 | 2 | 1280, 850 |
| 82 | 1335, 1150 | 2 | 1280, 850 |
| 25 | 1050 | 1 | 1245, 840 |
| 71 | 1050 | 1 | 1260, 840 |
| 13 | 1040 | 1 | 1260, 825 |
| 73 | 1045 | 1 | 1240, 840 |
| 79 | 1025 | 1 | 1245, 840 |
| 75 | 1040 | 1 | 1250, 840 |
| 77 | 1030 | 1 | 1240, 840 |
| 19 | 1050 | 1 | 1260, 840 |
| 50 | 1050 | 1 | 1250, 845 |
| 80 | 1055 | 1 | 1250, 840 |
| 83 | 1045 | 1 | 1250, 840 |
| 84 | 1320, 1130 | 2 | 1275, 840 |
| 86 | 1320, 1140 | 2 | 1280, 845 |
| 88 | 1310, 1120 | 2 | 1250, 840 |
| 91 | 1310, 1140 | 2 | 1270, 845 |
| 18 | 1315, 1150 | 2 | 1275, 845 |
| 85 | 1045 | 1 | 1250, 840 |
| 87 | 1040 | 1 | 1260, 820 |
| 89 | 1050 | 1 | 1240, 835 |
| 90 | 1045 | 1 | 1235, 840 |
| 93 | 1330, 1140 | 2 | 1280, 845 |
| 92 | 1310, 1140 | 2 | 1270, 845 |
| 95 | 1320, 1130 | 2 | 1260, 840 |
| 97 | 1320, 1130 | 2 | 1230, 840 |
| 99 | 1320, 1140 | 2 | 1270, 845 |
| 100 | 1320, 1120 | 2 | 1275, 845 |
| 104 | 1320, 1145 | 2 | 1280, 850 |
| 102 | 1310, 1140 | 2 | 1280, 845 |
| 94 | 1050 | 1 | 1250, 840 |
| 8 | 1045 | 1 | 1250, 840 |
| 96 | 1040 | 1 | 1240, 835 |
| 98 | 1040 | 1 | 1250, 835 |
| 101 | 1050 | 1 | 1250, 840 |
| 103 | 1050 | 1 | 1240, 840 |
| 105 | 1140, 1310 | 2 | 1270, 845 |
| 106 | 1140-1300 (SO 1050) | 2,1 | 1240, 890 |
| 107 | 1040 | 1 | 1250, 840 |
| 108 | 1140, 1320 | 2 | 1260, 840 |
| 109 | 1145, 1320 | 2 | 1280, 845 |
| 110 | 1140, 1300 | 2 | 1240, 840 |
| 111 | 1130, 1315 | 2 | 1230, 845 |
| 112 | 1040 | 1 | 1230, 840 |
| 113 | 1050 | 1 | 1245, 835 |
| 114 | 1130, 1315 | 2 | 1250, 840 |

EXAMPLE 115

To illustrate effectiveness of the described 2-sulfinyl and sulfonyl pyridine N-oxides as preemergent herbicides, 600 mg chemical is dissolved in 10 ml organic solvent (e.g. acetone) to which 30 mg conventional emulsifying agent (e.g. isooctyl polyethyoxyethanol, "Triton X100" [trademark]) is added. The solution is diluted to 100 ml with distilled water. Twenty milliliters of this 6000 ppm solution is diluted to 250 ppm with distilled water. The chemical is applied at the rate of 10 lbs/A (pounds per acre) by drenching 46 ml of the 250 ppm solution on the surface of soil in 4½ inch diameter plastic pots which had been sown with the following weed seeds: rough pigweed (*Amaranthus retroflexus* L.), purslane (*Portulaca oleracea* L.) or jimsonweed (*Datura stramonium* L.), tall morningglory (*Ipomea purpurea* (L.) Roth), crabgrass (*Digitaria ischaemum* (Schreb.) Muhl.), barnyardgrass (*Echinochloa crusgalli* (L.) Beauv.) and giant foxtail (*Setaria faberi* Herrm.). The percent control of the weeds compared to untreated checks is determined two weeks after treatment. Table III shows the results with the preemergence herbicides of the invention prepared in accordance with the above examples.

TABLE III

Herbicide activity of 2-Sulfinyl and 2-Sulfonyl Pyridine N-oxide

Percent Weed Control

| Ex. | Pigweed | Purslane[p] or Jimsonweed | Tall Morningglory | Barnyardgrass | Crabgrass | Giant Foxtail |
|---|---|---|---|---|---|---|
| 19 | 50 | 0[p] | 15 | 100 | 100 | 100 |
| 12 | 15 | 90[p] | 0 | 95 | 100 | 100 |
| 20 | 25 | 100[p] | 0 | 98 | 98 | 100 |
| 21 | 100 | 10 | 90 | 100 | 100 | 100 |
| 22 | 100 | 90 | 0 | 100 | 100 | 100 |
| 23 | 100 | 75 | 0 | 98 | 100 | 100 |
| 24 | 100 | 100 | 5 | 98 | 100 | 100 |
| 25 | 100 | 98 | 25 | 98 | 100 | 100 |
| 1 | 100 | 100 | 100 | 100 | 100 | 100 |
| 26 | 20 | 0 | 0 | 90 | 100 | 95 |
| 27 | 50 | 0 | 0 | 98 | 100 | 100 |
| 28 | 98 | 0 | 0 | 98 | 100 | 98 |
| 29 | 0 | 0 | 0 | 98 | 100 | 100 |
| 30 | 95 | 0 | 0 | 60 | 90 | 90 |
| 31 | 100 | 0 | 0 | 100 | 100 | 100 |
| 11 | 85 | 80 | 25 | 98 | 100 | 100 |
| 32 | 95 | 95 | 20 | 90 | 95 | 95 |
| 2 | 100 | 0 | 20 | 95 | 100 | 100 |
| 19 | 100 | 80 | 80 | 95 | 100 | 100 |
| 33 | 100 | 50 | 25 | 90 | 100 | 100 |
| 34 | 100 | 20 | 0 | 95 | 100 | 100 |
| 9 | 100 | 100 | 95 | 95 | 100 | 100 |
| 35 | 100 | 0 | 0 | 95 | 100 | 100 |
| 36 | 98 | 0 | 0 | 98 | 98 | 95 |
| 37 | 0 | 0 | 0 | 90 | 90 | 75 |
| 38 | 100 | 0 | 0 | 100 | 100 | 100 |
| 39 | 0 | 25 | 0 | 85 | 85 | 85 |
| 8 | 100 | 0 | 94 | 100 | 100 | 100 |
| 40 | 0 | 0 | 0 | 75 | 98 | 100 |

TABLE III-continued

Herbicide activity of 2-Sulfinyl and 2-Sulfonyl Pyridine N-oxide
Percent Weed Control

| Ex. | Pigweed | Purslane[P] or Jimson-weed | Tall Morning-glory | Barnyard-grass | Crab-grass | Giant Foxtail |
|---|---|---|---|---|---|---|
| 41 | 100 | 0 | 0 | 95 | 100 | 100 |
| 42 | 100 | 70 | 0 | 90 | 100 | 100 |
| 43 | 75 | 0 | 0 | 95 | 98 | 98 |
| 44 | 100 | 0 | 0 | 98 | 100 | 100 |
| 45 | 80 | 0 | 0 | 90 | 90 | 90 |
| 46 | 100 | 0 | 20 | 98 | 100 | 100 |
| 47 | 95 | 0 | 0 | 98 | 98 | 98 |
| 48 | 100 | 65 | 0 | 98 | 98 | 98 |
| 49 | 100 | 50 | 0 | 98 | 98 | 98 |
| 10 | 98 | 40 | 70 | 100 | 100 | 100 |
| 50 | 98 | 0 | 0 | 95 | 98 | 98 |
| 51 | 98 | 0 | 30 | 98 | 100 | 100 |
| 52 | 95 | 0 | 10 | 98 | 98 | 98 |
| 53 | 85 | 0 | 65 | 98 | 98 | 98 |
| 54 | 40 | 0 | 15 | 98 | 98 | 98 |
| 55 | 100 | 0 | 0 | 100 | 100 | 100 |
| 56 | 100 | 0 | 50 | 98 | 98 | 100 |
| 57 | 100 | 25 | 40 | 98 | 98 | 98 |
| 58 | 100 | 20 | 0 | 95 | 98 | 98 |
| 59 | 100 | 0 | 85 | 98 | 98 | 100 |
| 60 | 100 | 0 | 85 | 98 | 98 | 100 |
| 61 | 95 | 10 | 25 | 95 | 98 | 98 |
| 62 | 100 | 0 | 35 | 95 | 98 | 98 |
| 63 | 100 | 0 | 0 | 90 | 98 | 98 |
| 64 | 100 | 0 | 0 | 85 | 85 | 90 |
| 65 | 100 | 0 | 35 | 98 | 100 | 100 |
| 66 | 100 | 0 | 50 | 95 | 98 | 100 |
| 67 | 100 | 0 | 0 | 98 | 98 | 98 |
| 4 | 100 | 25 | 0 | 100 | 100 | 100 |
| 68 | 100 | 0 | 0 | 100 | 100 | 100 |
| 69 | 100 | 0 | 0 | 100 | 100 | 100 |
| 70 | 95 | — | — | 60 | 50 | 30 |
| 71 | 100 | 0 | 0 | 100 | 100 | 100 |
| 15 | 100 | 100 | 15 | 100 | 100 | 100 |
| 13 | 100 | 75 | 100 | 100 | 100 | 100 |
| 72 | 95 | 0 | 0 | 95 | 98 | 98 |
| 73 | 100 | 0 | 0 | 98 | 98 | 98 |
| 74 | 0 | 50 | 0 | 98 | 98 | 100 |
| 75 | 0 | 0 | 0 | 98 | 98 | 98 |
| 76 | 0 | 0 | 90 | 98 | 98 | 98 |
| 5 | 95 | 0 | 50 | 98 | 98 | 98 |
| 77 | — | — | — | 100 | 100 | 100 |
| 78 | 0 | 0 | 0 | 98 | 98 | 98 |
| 16 | 100 | 85 | 98 | 100 | 100 | 100 |
| 6 | 95 | 80 | 95 | 100 | 100 | 100 |
| 79 | — | 25 | — | 100 | 100 | 100 |
| 7 | — | 35 | 0 | 100 | 100 | 100 |
| 80 | 0 | 0 | 0 | 98 | 100 | 100 |
| 17 | 0 | 0 | 0 | 98 | 100 | 100 |
| 81 | 0 | 0 | 0 | 98 | 100 | 100 |
| 82 | 0 | 0 | 0 | 50 | 75 | 100 |
| 83 | 100 | 0 | 0 | 100 | 100 | 100 |
| 84 | 100 | 0 | 0 | 100 | 100 | 100 |
| 85 | 100 | 0 | 0 | 98 | 100 | 100 |
| 86 | 100 | 100 | 0 | 100 | 100 | 100 |
| 87 | 100 | 0 | 0 | 98 | 100 | 100 |
| 88 | 100 | 0 | 0 | 100 | 100 | 100 |
| 89 | — | — | — | 100 | 100 | 100 |
| 90 | 0 | 0 | 0 | 80 | 80 | 80 |
| 91 | 50 | 0 | 0 | 90 | 85 | 85 |
| 18 | 100 | 30 | 100 | 100 | 100 | 100 |
| 92 | 100 | 95 | 75 | 98 | 98 | 98 |
| 93 | 100 | 95 | 65 | 98 | 98 | 98 |
| 94 | 100 | 60 | 85 | 100 | 100 | 100 |
| 8 | 100 | 0 | 100 | 100 | 100 | 100 |
| 95 | 100 | 0 | 0 | 95 | 100 | 100 |
| 96 | 100 | 0 | 0 | 100 | 100 | 100 |
| 97 | 100 | 0 | 0 | 100 | 100 | 100 |
| 98 | 100 | 0 | 50 | 100 | 100 | 100 |
| 99 | 100 | 0 | 0 | 100 | 100 | 100 |
| 100 | 100 | 0 | 0 | 95 | 100 | 100 |
| 101 | 100 | 0 | 80 | 100 | 100 | 100 |
| 102 | 100 | 100 | 100 | 100 | 100 | 100 |
| 103 | 30 | 30 | 0 | 30 | 20 | 20 |
| 104 | 0 | 0 | 0 | 30 | 10 | 10 |
| 105 | 30 | 30 | 0 | 85 | 100 | 100 |
| 106 | 0 | 0 | 0 | 70 | 100 | 100 |
| 107 | 100 | — | 0 | 95 | 100 | 95 |
| 108 | 100 | — | 0 | 95 | 98 | 98 |
| 109 | 0 | — | 95 | 50 | 95 | 95 |
| 110 | 0 | 0 | 5 | 98 | 95 | 95 |
| 111 | 90 | 0 | 62 | 95 | 95 | 95 |
| 112 | 20 | 0 | 0 | 80 | 80 | 80 |
| 113 | 0 | 0 | 25 | 95 | 95 | 95 |
| 114 | 100 | 0 | 25 | 98 | 98 | 98 |

EXAMPLE 116

Selectivity of a herbicide is desirable since it allows control of weeds growing among desirable crop plants. To illustrate the usefulness of the compounds of this invention as selective preemergence herbicides, 0.8 g chemical is dissolved in 50 ml organic solvent such as acetone containing 25 mg conventional emulsifying agent (e.g. isoctyl polyethoxyethanol, Triton X-100), and sprayed at the rate of 4 lbs active in 30 gallons of water per acre onto the surface of soil contained in 15 inch × 20 inch flats. Weed and crop seeds were sown into the soil prior to treatment. The percent weed control and crop injury were evaluated 3 weeks after treatment. Table IV illustrates the usefulness of these chemicals as selective preemergence herbicides.

TABLE IV

Selective Preemergence Herbicide Test

| | Percent Crop Injury | | | | | | Percent Weed Control | | | | |
|---|---|---|---|---|---|---|---|---|---|---|---|
| Ex. | Flax | Alfalfa | Cotton | Soybeans | Peanuts | Pigweed | Purslane | Wild Oats | Texas Panicum | Giant Foxtail | Barnyardgrass |
| 1 | 0 | 10 | 0 | 0 | 0 | 98 | 100 | 100 | 100 | 100 | 100 |
| 14 | 0 | 0 | 0 | 0 | 0 | 70 | 100 | 100 | 100 | 100 | 100 |
| 9 | 50 | 10 | 0 | 75 | 0 | 100 | 100 | 100 | 100 | 100 | 100 |

EXAMPLE 117

To illustrate efficacy at 2 lb/A, 50 ppm solutions (Example 115) were drenched onto the soil surface at the rate of 46 ml per 4½ inch diameter pot. The seeds of several weed species were sown into the soil of each pot prior to chemical application. The percent control of weeds compared to untreated checks was determined two weeks after emergence. Table V shows the results of efficacy tests at 2 lb/A.

TABLE V

Herbicide Activity at 2 Pounds per Acre
Percent Weed Control

| Ex. | State of Oxidation | Barnyardgrass | Yellow Foxtail | Crabgrass | Green Foxtail | Wild Oats | Texas or Fall Panicum |
|---|---|---|---|---|---|---|---|
| 58 | Sulfoxide | 90 | 90 | 80 | 50 | 0 | 100 |
| 21 | Sulfone | 100 | 100 | 90 | 75 | 100 | 100 |
| 61 | Sulfoxide | 90 | 70 | 85 | 70 | 0 | 95 |
| 22 | Sulfone | 100 | 100 | 100 | 100 | 90 | 100 |
| 25 | Sulfoxide | 100 | 100 | 100 | 90 | 90 | 100 |
| 23 | Sulfone | 95 | 100 | 100 | 100 | 90 | 100 |
| 46 | Sulfoxide | 100 | 100 | 100 | 100 | 90 | 100 |

TABLE V-continued

Herbicide Activity at 2 Pounds per Acre
Percent Weed Control

| Ex. | State of Oxidation | Barn-yard grass | Yellow Fox-tail | Crab-grass | Green Fox-tail | Wild Oats | Texas or Fall Pani-cum |
|---|---|---|---|---|---|---|---|
| 1 | Sulfone | 100 | 100 | 100 | 100 | 100 | 100 |
| 59 | Sulfoxide | 95 | 95 | 95 | 95 | 0 | 100 |
| 11 | Sulfone | 100 | 100 | 100 | 100 | 95 | 100 |
| 56 | Sulfoxide | 100 | 100 | 100 | 95 | 50 | 100 |
| 2 | Sulfone | 100 | 100 | 100 | 100 | 85 | 100 |
| 51 | Sulfoxide | 95 | 95 | 90 | 90 | 20 | 100 |
| 33 | Sulfone | 90 | 95 | 95 | 60 | 40 | 100 |
| 55 | Sulfone | 85 | 70 | 100 | 70 | 20 | 100 |

TABLE VI

Herbicide Activity at ½ lb/A.
Percent Weed Control

| Ex. | State of Oxidation | Barn-yard grass | Yellow Fox-tail | Crab-grass | Green Fox-tail | Wild Oats | Texas or Fall Pani-cum |
|---|---|---|---|---|---|---|---|
| 57 | Sulfoxide | 90 | 80 | 85 | 40 | 0 | 100 |
| 31 | Sulfone | 90 | 95 | 100 | 50 | 30 | 100 |
| 3 | Sulfoxide | 100 | 100 | 100 | 100 | 90 | 100 |
| 14 | Sulfone | 100 | 100 | 100 | 95 | 60 | 100 |
| 10 | Sulfoxide | 95 | 100 | 100 | 85 | 20 | 100 |
| 34 | Sulfone | 95 | 100 | 85 | 80 | 50 | 100 |

EXAMPLE 118

Listed below are non-limiting examples of formulations which can be used in this invention.

1. 9.6% active one lb/gallon emulsifiable concentrate
   a. 2-(2,5-Dimethylphenylmethylsulfonyl)-pyridine N-oxide — 0.6 gm
   b. Blend of oil soluble sulfonates with polyoxyethylene ethers (Emcol N139-BU [trademark] Witco Chemical Corp.; e.g. nonylphenol polyoxyethylene plus calcium dodecylbenzene sulfonate) — 0.55 gm
   c. Chloroform — 2.4 gm
   d. Benzaldehyde — 2.7 gm
2. 11.3% active one lb/gallon soluble concentrate
   a. 2-(Phenylmethylsulfonyl)pyridine N-oxide — 24.0 gm
   b. Blend of oil soluble sulfonates with poly-oxyethylene ethers (Emcol N5003 [trademark] Witco Chemical Corp.; e.g., sodium lignin sulfonate plus polycondensate of ethylene oxide, propylene oxide and propylene glycol. — 12.0 gm
   c. Phenol (90% aqueous solution) — 178.5 gm
3. 50% active wettable powder
   a. 2-(2,5-Dimethylphenylmethylslfonyl)-pyridine N-oxide — 300 gm
   b. Alkylaryl polether alcohol OPE (octyl-phenoxy polyethoxy ethanol) (Trition X-120 [trademark], Rohm & Hass) — 6 gm
   c. Sodium N-methyl-N-palmitoyl taurate (Igepon TN-74 [trademark] GAF Corp.) — 6 gm
   d. Polymerized sodium salts of alkyl naptha-lene sulfonic acid [Daxed 11 [trademark] Dewey & Almy Chemical Company] — 12 gm
   e. Kaolinite clay (Dixie Clay [trademark]) — 84 gm
   f. Hydrated amorphous silica (Hi Sil 233 [trademark]) — 192 gm
4. 5% active granule
   a. 2-(2-,5-Dimethylphenylmethylsulfonyl)-pyridine N-oxide — 1.0 gm
   b. Methylene chloride — 9.0 gm
   c. Above solution sprayed onto hydrated magnesium aluminum Silicate 25/50 mesh (Attaclay [trademark]) — 19.0 gm

We claim:

1. A method of controlling weeds comprising applying, to a locus at which it is desired to control weeds, a herbicidally effective amount of a 2-sulfinyl or 2-sulfonyl pyridine N-oxide compound of the formula:

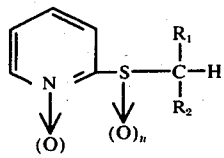

where
  $n$ is 1 or 2;
  $R_1$ is hydrogen, alkyl having 1 to 3 carbon atoms or phenyl;
  $R_2$ has one of the following values when $R_1$ is hydrogen:
    benzyl, styryl, naphthyl, methylnaphthyl, phenyl, substituted phenyl with 1 to 5 substituents which may be the same or different and are selected from alkyl having 1 to 3 carbon atoms, halogen, nitro, cyano, alkoxy having 1 to 2 carbon atoms and trifluoromethyl;
  $R_2$ has one of the following values when $R_1$ is other than hydrogen:
    naphthyl, phenyl, substituted phenyl with 1 to 3 substituents which may be the same or different and are selected from alkyl having 1 to 2 carbon atoms, halogen, nitro, and methyl sulfonyl.

2. A method as in claim 1 in which $n$ is 1.
3. A method as in claim 1 in which $n$ is 2.
4. A method as in claim 1 in which $R_1$ is hydrogen or methyl.
5. A method as in claim 1 in which $R_2$ is selected from the group consisting of phenyl, phenyl substituted with from 1 to 3 methyl groups, phenyl substituted with from 1 to 3 halogens and 2-naphthyl.
6. A method as in claim 1 in which $R_1$ is hydrogen and $R_2$ is selected from the group consisting of phenyl substituted with from 1 to 3 methyl groups and phenyl substituted with from 2 to 3 chlorines.
7. A method as in claim 1 in which $R_1$ is methyl and $R_2$ is selected from the group consisting of phenyl, phenyl substituted with 1 or 2 methyl groups, monohalophenyl and 2-naphthyl.
8. A method as in claim 1 in which the said compound is selected from the group consisting of
  2-(2,5-dimethylphenylmethylsulfonyl)pyridine N-oxide,
  2-(2,4,6-trimethylphenylmethylsulfonyl)pyridine N-oxide,
  2-(2,6-dichlorophenylmethylsulfonyl)pyridine N-oxide,
  2-(2,4-dichlorophenylmethylsulfinyl)pyridine N-oxide,
  2-(2,6-dichlorophenylmethylsulfinyl)pyridine N-oxide,
  2-(1-[4-methylphenyl]ethylsulfonyl)pyridine N-oxide,
  2-(2,3,6-trichlorophenylmethylsulfonyl)pyridine N-oxide,
  2-(2-methylphenylmethylsulfonyl)pyridine N-oxide,
  2-(1-[4-fluorophenyl]ethylsulfonyl)pyridine N-oxide,
  2-(1-[2,5-dimethylphenyl]ethylsulfonyl)pyridine N-oxide,
  2-(2,3,6-trichlorophenylmethylsulfinyl)pyridine N-oxide,
  2-(1-phenylethylsulfonyl)pyridine N-oxide,
  2-(1-[2-naphthyl]ethylsulfonyl)pyridine N-oxide,
  2-(1-[4-chlorophenyl]ethylsulfonyl)pyridine N-oxide,
  2-(1-[4-bromophenyl]ethylsulfonyl)pyridine N-oxide, 2-(2,3,6-trimethylphenylmethylsulfonyl)pyridine N-oxide, and 2-(2,3,6-trimethylphenylmethylsulfinyl)pyridine N-oxide.

9. A method as in claim 1 in which the said compound is selected from the group consisting of 2-(2,5-dimethylphenylmethylsulfonyl)pyridine N-oxide,
2-(2,6-dichlorophenylmethylsulfinyl)pyridine N-oxide,
2-(1-[2,5-dimethylphenyl]ethylsulfonyl)pyridine N-oxide,
2-(2,4,6-trimethylphenylmethylsulfonyl)pyridine N-oxide,
2-(1-[2-naphthyl]ethylsulfonyl)pyridine N-oxide,
2-(1-[4-chlorophenyl]ethylsulfonyl)pyridine N-oxide,
2-(1-[4-methylphenyl]ethylsulfonyl)pyridine N-oxide, and
2-(2,3,6-trimethylphenylmethylsulfinyl)pyridine N-oxide.

10. A method as in claim 1 in which the said compound is 2-(2,5-dimethylphenylmethylsulfonyl)pyridine N-oxide.

11. A method as in claim 1 in which the said compound is 2-(2,6-dichlorophenylmethylsulfinyl)pyridine N-oxide.

12. A method as in claim 1 in which the said compound is 2-(1-[2,5-dimethylphenyl]ethylsulfonyl)pyridine N-oxide.

13. A method as in claim 1 in which the said compound is 2-(2,4,6-trimethylphenylmethylsulfonyl)pyridine N-oxide.

14. A method as in claim 1 in which the said compound is 2-(1-[2-naphthyl]ethylsulfonyl)pyridine N-oxide.

15. A method as in claim 1 in which the said compound is 2-(1-[4-chlorophenyl]ethylsulfonyl)pyridine N-oxide.

16. A method as in claim 1 in which the said compound is 2-(1-[4-methylphenyl]ethylsulfonyl)pyridine N-oxide.

17. A method as in claim 1 in which the said compound is 2-(2,3,6-trimethylphenylmethylsulfinyl)pyridine N-oxide.

* * * * *